United States Patent [19]

Stütz

[11] Patent Number: 4,542,022

[45] Date of Patent: Sep. 17, 1985

[54] SILYL-ALKYN-EN-YLAMINE DERIVATIVES

[75] Inventor: Anton Stütz, Maria Enzersdorf, Austria

[73] Assignee: Sandoz Ltd., Basel, Switzerland

[21] Appl. No.: 340,981

[22] Filed: Jan. 20, 1982

[30] Foreign Application Priority Data

Jan. 26, 1981 [CH] Switzerland .......................... 476/81

[51] Int. Cl.[4] ............................ C07F 7/08; C07F 7/10
[52] U.S. Cl. .................................... 514/63; 556/413; 549/4; 549/214; 548/406; 546/14
[58] Field of Search .................... 556/413; 549/214, 4; 548/406; 546/14; 424/184

[56] References Cited

U.S. PATENT DOCUMENTS 3,946,060  3/1976  Metcalf et al. ...................... 556/413
4,088,668  5/1978  Metcalf et al. .................. 556/413 X Primary Examiner—Paul F. Shaver
Attorney, Agent, or Firm—Gerald D. Sharkin; Richard E. Vila; Frederick H. Weinfeldt

[57] ABSTRACT

Silyl-alkyn-en-ylamine derivatives which possess pharmaceutical in particular anti-mycotic activity.

5 Claims, No Drawings

SILYL-ALKYN-EN-YLAMINE DERIVATIVES

The present invention concerns new organic compounds, in particular silyl-alkyn-en-ylamine derivatives, processes for their production and their use.

All formulae referred to in the specification and claims are as shown hereinafter on the formula sheets and reaction schemes.

The invention concerns more particularly a compound of formula I
wherein
$R_1$ represents a group of formula IIa, IIb, IIc or IId
$R_2$ represents hydrogen or lower alkyl or,
$R_1$ and $R_2$ together with carbon atom to which they are attached represent a group of formula IIe,
$R_3$ and $R_4$ represent independently hydrogen or lower alkyl or, when $R_1$ represents a group of formula IIa, IIb, IIc or IId, can also represent together a straight-chain $C_3$–$C_5$ alkylene bridge,
$R_8$, $R_9$ and $R_{10}$ represent independently lower alkyl or lower alkenyl, and
m is 0, 1 or 2, whereby in the formulae IIa to IIe
  $R_5$ and $R_6$ represent independently hydrogen, halogen, lower alkyl, lower alkoxy or trifluoromethyl,
  X represents oxygen, sulphur, —O—$CH_2$—, —S—$CH_2$, —$CH_2$— or —N($R_7$)—, wherein $R_7$ represents hydrogen or lower alkyl,
  p is 1, 2 or 3 and
  s is 3, 4 or 5,
or an acid addition salt thereof.

According to the invention, the compounds of formula I may be obtained by
(a) reacting a compound of formula IV wherein $R_1$, $R_2$, $R_3$ and $R_4$ are as defined above, after deprotonisation with an appropriate base with a compound of formula V, wherein $R_8$, $R_9$, $R_{10}$ and m are as defined above and A represents halogen,
(b) reacting a compound of formula VI, wherein $R_1$, $R_2$, $R_3$ and $R_4$ are as defined above, with a compound of formula VII wherein $R_8$, $R_9$, $R_{10}$ and m are as defined above and B represents a leaving group.

Process (a) can be carried out in conventional manner, for example in a solvent, inert under the reaction conditions, such as a cyclic ether such as tetrahydrofurane and at temperatures between −80° C. and room temperature. A is preferably chlorine or bromine. As base, necessary for the deprotonation of the compound of formula IV, every strong base able to deprotonize an acetylenehydrogen may be used such as butyllithium.

Process (b) can be carried out in conventional manner, for example in a solvent, inert under the reaction conditions, such as an aromatic hydrocarbon such as benzene or toluene, a cyclic ether, such as dioxane and tetrahydrofuran or a carboxylic acid dialkylamide, such as dimethylformamide and at temperatures between room temperature (which is preferred) and the boiling point of the reaction mixture.

Leaving group B, can for example be halogen preferably chlorine or bromine, or an organic sulphonyloxy group having 1 to 10 carbon atoms, e.g. alkylsulphonyloxy, preferably having 7 to 10 carbon atoms such as tosyloxy. The reaction is conveniently carried out, when appropriate, in the presence of an acid binding agent, e.g. an alkali or alkaline earth metal hydroxide or carbonate such as sodium carbonate.

The compounds of formula I may be converted in conventional manner into their acid addition salts and vice versa. Suitable acid addition salts are e.g. hydrochloride, hydrogen fumarate or naphthaline-1,5-disulphonate.

The compounds of the formula I and their intermediates can be obtained in form of isomeric mixtures of the various cis/trans isomers which can be separated according to established methods.

Any lower alkyl or lower alkoxy radical has preferably 1 to 4 carbon atoms, especially 2 or 1 carbon atoms. Any lower alkenyl radical has preferably 3 to 6 carbon atoms, specially 3 or 4, e.g. allyl. In the definitions of $R_5$ and $R_6$, halogen stands for fluorine, chlorine or bromine.

The starting materials of formula IV are in part new and can be prepared, for example, by reacting a compound of formula VI with a compound of formula VIII, wherein B is as defined above. This process can be performed analogously to process (b) described above.

The starting materials or formula VI are in part new and can be prepared, for example, by reacting in conventional manner a compound of formula IX, wherein $R_1$, $R_2$, $R_3$ and A are as defined above, with a compound of formula X, wherein $R_4$ is as defined above.

The starting materials of formula VII are in part new and can be prepared analogously to T. Masamune et. al., Bull. Chem. Soc. Jap. 52/135–141 (1979).

The remaining intermediate compounds are either known or can be prepared according to known methods or as hereinbefore described.

The compounds of formula I exhibit chemotherapeutic activity. In particular, they exhibit antimycotic activity, as indicated in vitro in various families and types of mycetes, including Trichophyton spp, Aspergillus spp, Microsporum spp, *Sporotrychium schenkii* and Candida spp, at concentrations of, for example 0.1 to 25 μg/ml, and in vivo in the experimental skin mycosis model in guinea pigs. In this model, guinea pigs are infected by sub-cutaneous applications of Trichophyton quinckeanum. The test substance is administered daily for 7 days beginning 24 hours after the infection either on local application by rubbing the test substance (taken up in polyethylene glycol) on the skin surface, or perorally or sub-cutaneously, the test substance being administered as a suspension. The activity is shown on local application at concentrations of for example 0.1 to 2%. The oral activity is shown in vivo in the guinea-pig-Trichophytosis model at dosages of, for example, 2 to 70 mg/kg.

The compounds may therefore be used as antimycotic agents. For this use, the effective dosage will, of course, vary depending on the particular compound employed, the mode of administration and the treatment desired. However, in general, satisfactory results can be obtained when the compounds are administered at a daily dosage of from about 1 to 30 mg/kg of animal body weight, suitably given in divided doses two to four times daily. For most large mammals, the total daily dosage is from about 70 to 2000 mg and dosage forms suitable for internal administration comprise about 17.5 to 1000 mg of the compound in admixture with a solid or liquid chemotherapeutical carrier or diluent.

The compounds of formula I may be administered in similar manner to known standards for use in such indications e.g. Griseofulvin and Tolnaftal.

The suitable daily dosage for a particular compound will depend on a number of factors such as its relative potency of activity. It has, for example, been determined in the guinea-pig-Trichophytosis model that the preferred compound of this invention namely trans-N-(1-naphthylmethyl)-N-methyl-5-trimethylsilyl-pent-2-en-4-ynyl-1-amine has a curative dose (i.e. the dose sufficient to cure guinea pigs infected with Trichophyton mentagrophytes var.quinckeanum 158 of all mycological symptoms) of $9\times 6$ mg/kg/day as compared to $9\times 70$ mg/kg/day for Griseofulvin. It is therefore indicated that these compounds may be administered at similar or lower dosages than conventionally employed for Griseofulvin.

The compounds may be used in free base form or in the form of chemotherapeutically acceptable acid addition salts. Such salt forms exhibit the same order of activity as the free base forms. Suitable such salt forms are e.g. hydrochloride, hydrogen fumarate or naphthaline-1,5-disulphonate.

The compounds may be admixed with conventional chemotherapeutically acceptable diluents and carriers, and, opionally, other excipients and administered in such forms as tablets or capsules. The compounds may alternatively be administered topically in such conventional forms as ointments or creams or parenterally. The concentrations of the active substance will of course vary depending on the compound employed, the treatment desired and the nature of the form etc. In general, however, satisfctory results are obtained e.g. in topical application forms at concentrations of from 0.05 to 5, in particular 0.1 to 1 wt%.

Such compositions also form part of the invention.

Preferred meanings for the substituents are as follows:

$R_2$, $R_3$ and $R_6$ = hydrogen,
$R_4$ = alkyl preferably methyl,
$R_5$ = hydrogen or halogen e.g. chlorine,
$R_8$, $R_9$ and $R_{10}$ = alkyl preferably methyl,
m = is 0,
p, s = number selected to form 5- or 6-membered ring,
$R_1$ = IIa or IIb,
X = O or S
and combinations of these.

The double bond adjacent to the nitrogen atom preferably has the trans-configuration.

A particularly preferred single compound is: trans-N-(1-naphthylmethyl)-N-methyl-5-trimethylsilyl-pent-2-en-4-ynyl-1-amine.

The following Examples illustrate the invention whereby all temperatures are in degrees centigrade.

EXAMPLE 1

Trans-N-(1-naphthylmethyl)-N-methyl-5-trimethylsilyl-pent-2-en-4-ynyl-1-amine (process a); compound no. 1)

10 g of trans-N-(1-naphthylmethyl)-N-methyl-pent-2-en-4-ynyl-1-amine are disolved in absolute tetrahydrofuran reacted under cooling with 35 ml of a 15% solution of butyllithium in hexane and then, at −20°, with 5.4 ml of trimethylchlorosilane and stirred overnight at room temperature. The reaction mixture is poured onto ice, extracted with dichloromethane and the organic phase washed with saturated aqueous $NaHCO_3$, dried and concentrated on a rotary evaporator. The analytically pure title product is obtained after bulb distillation (150°/1.33 Pascal), or chromatography over kieselgel (eluant toluent/ethylacetate; 9/1) as a colourless oil.

EXAMPLE 2

Trans-N-(1-naphthylmethyl)-5-trimethylsilyl-pent-2-en-4-ynyl-1-amine (process b; compound no. 2)

10.6 g of trans-1-bromo-trimethylsilyl-pent-2-en-4-yne are added dropwise to a mixture of 15.3 g 1-naphthylmethylamine, 5.2 g of $Na_2CO_3$ and 100 ml of dimethylformamide and stirred overnight. The reaction mixture is filtered and the solvent removed in vacuum. The residue is partitioned between ether and saturated aqueous $NaHCO_3$ and the organic phase dried and concentrated on a rotary evaporator. After chromatography over kieselgel (eluant toluene/ethylacetate; 4/1) the title substance is obtained as an oil.

Analogously to Example 1 or 2 or as otherwise described hereinbefore, the following compounds of formula I can be obtained ($R_2$ and $R_3$ = H; $R_4$ = $CH_3$).

| Cmpd. No. | $R_1$ | $R_5$ | Isomer | phys. chem. data |
| --- | --- | --- | --- | --- |
| 3 | naphthyl | $-Si(C_2H_5)_3$ | trans | b.p.: 170°/13/Pascal |
| 4 | " | $-Si(CH_3)_2-C(CH_3)_3$ | trans | b.p.: 160–165°/13 Pascal |
| 5 | " | $-Si(CH_3)_2-CH_2-CH=CH_2$ | trans | oil |
| 6 | benzothiophene | $-Si(CH_3)_3$ | trans | oil |

-continued

| Cmpd. No. | R₁ | R₅ | Isomer | phys. chem. data |
|---|---|---|---|---|
| 7 | benzothiophene | " | trans | oil |
| 8 | methyl-tetrahydronaphthalene | " | trans | oil |
| 9 | 6-chloro-2H-1-benzopyran | —Si(CH₃)₃ | E | oil |

Proceeding analogously to Example 1 or 2 or as otherwise described hereinbefore, the following compound can also be obtained trans-2-(1-naphthyl)-1-(5-trimethylsilyl-pent-2-en-4-in-1-yl)-piperidine (compound no. 10)

residue is partitioned between ether and saturated aqueous NaHCO₃ and the organic phase dried and concentrated on a rotary evaporator. After chromatography on kieselgel (eluant: toluene/ethylacetate; 4/1) the title product is obtained m.p. 150°–155° (hydrochloride.)

NMR-SPECTRA (DCCl₃,RT, TMS):

| Cmpd. | Spectra |
|---|---|
| 1 | δ = 8,2–8,4 (m, 1H); 7,7–8,0 (m, 2H); 7,4–7,65 (m, 4H); 6,35 (dt, J = 17 u. 2 × 7 Hz, 1H); 5,72 (dt, J = 17 u. 2 × 1,5 Hz, 1H); 3,92 (s, 2H); 3,15 (dd, J = 7 u. 1,5 Hz, 2H); 2,25 (s, 3H); 0,2 (s, 9H). |
| 2 | δ = 8,05–8,2 (m, 1H); 7,7–7,95 (m, 2H); 7,35–7,65 (m, 4H); 6,36 (dt, J = 16 u. 2 × 6 Hz, 1H); 5,74 (dt, = J 16 u. 2 × 1,5 Hz, 1H); 4,22 (s, 2H); 3,42 (dd, J = 6 u. 1,5 Hz, 2H); 1,5 (s, NH); 0,18 (s, 9H). |
| 3 | δ = 8,2–8,4 (m, 1H); 7,7–7,95 (m, 2H); 7,4–7,65 (m, 4H); 6,36 (dt, J = 17 u. 2 × 7 Hz, 1H); 5,74 (dt, J = 17 u. 1,5 Hz, 1H); 3,9 (s, 2H); 3,15 (dd, J = 7 u. 1,5 Hz, 2H); 2,22 (s, 3H); 0,85–1,15 (m, 9H); 0,45–0,8 (m, 6H). |
| 4 | δ = 8,2–8,4 (m, 1H); 7,7–7,95 (m, 2H); 7,35–7,6 (m, 4H); 6,35 (dt, J = 17 u. 2 × 7 Hz, 1H); 5,70 (dt, J = 17 u. 2 × 1,5 Hz, 1H); 3,9 (s, 2H); 3,13 (dd, J = 7 u. 1,5 Hz, 2H); 2,22 (s, 3H); 0,95 (s, 9H); 0,12 (s, 6H). |
| 5 | δ = 8,2–8,35 (m, 1H); 7,6–7,9 (m, 2H); 7,4–7,6 (m, 4H); 6,33 (dt, J = 17 u. 2 × 7 Hz, 1H); 5,6–6,1 (m, 2H); 4,75–5,05 (m, 2H); 3,9 (s, 2H); 3,14 (dd, J = 7 u. 1,5 Hz, 2H); 2,22 (s, 3H); 1,55–1,7 (m, 2H); 0,16 (s, 6H). |
| 6 | δ = 7,7–7,85 (m, 1H); 7,25–7,5 (m, 4H); 6,38 (dt, J = 16 u. 2 × 6 Hz, 1H); 6,75 (dt, J = 16 u. 2 × 1,5 Hz, 1H); 3,78 (s, 2H); 3,14 (dd, J = 6 u. 1,5 Hz, 2H); 2,24 (s, 2H); 0,18 (s, 9H). |
| 7 | δ = 7,8–8,1 (m, 2H); 7,25–7,55 (m, 3H); 6,35 (dt, J = 16 u. 2 × 6 Hz, 1H); 5,74 (dt, J = 16 u. 2 × 1,5 Hz, 1H); 3,75 (s, 2H); 3,15 (dd, J = 6 u. 1,5 Hz); 2,28 (s, 3H); 0,24 (s, 9H). |
| 8 | δ = 6,9–7,15 (m, 3H); 6,28 (dt, J = 16 u. 2 × 6,5 Hz, 1H); 5,68 (dt, J = 16 u. 2 × 1,5 Hz, 1H); 3,4 (s, 2H); 3,05 (dd, J = 6,5 u. 1,5 Hz, 2H); 2,6–2,9 (m, 2H); 2,16 (s, 3H); 1,65–1,9 (m, 2H); 0,18 (s, 9H). |
| 9 | δ = 7,45 (d, J = 3 Hz, 1H); 7,12 (dd, J₁ = 3 Hz, J₂ = 10 Hz, 1H); 6,77 (d, J = 10 Hz, 1H); 6.32 (dt, J₁ = 7 Hz, J₂ = 18 Hz, 1H); 5,6–5,9 (m, 2H); 4,74–4,86 (m, 2H); 3,20–3,28 (m, 2H); 3,12 (dd, J₁ = 2 Hz, J₂ = 7 Hz, 2H); 2,25 (s, 3H); 0,21 (s, 9H). |
| 10 | δ = 8,2–8,9 (br, 1H); 7,4–8,0 (m, 6H); 6,0–6,4 (ddd, J = 5, 8 u. 16 Hz, 1H); 5,58 (dbr, J = 16 Hz, 1H); 3,7–4,0 (br, 1H); 3,1–3,4 (m, 2H); 2,54 (d,d, J = 8 u. 15 Hz, 1H); 1,4–2,3 (m, 7H); 0,2 (s, 9H) |

The required starting materials can be prepared for example as follows.

(A)
trans-N-(1-naphthylmethyl)-N-methyl-pent-2-en-4-ynyl-1-amine (for i.a. Examples 1, 3, 4 and 5).

16 g of 1-mesyloxy-pent-2-en-4-yne are added dropwise to a mixture of 17.1 g of N-(1-naphthylmethyl)-N-methylamine, 10.5 g of Na₂CO₃ and 100 ml of dimethylformamide and stirred overnight. The reaction mixture is filtered and the solvent removed in vacuum. The (B)
trans-N-(6-chloro-2H-1-benzopyran-4-yl-methyl)-N-methyl-pent-2-en-4-ynyl-1-amine (for Example 9)

(a) 6-chloro-4-hydroxymethyl-2H-1-benzopyrane
A mixture of 19.5 g of 4-chlorophenyl-(4-hydroxybut-2-ynyl)ether and 60 ml of diethylaniline are refluxed for 2 hours under an inert gas (bath temperature ca. 230°). The main portion of the diethylaniline is distilled off in vacuum (1300 Pascal) and the residue poured onto ice/water. The resulting mixture is acidified to pH 4–5 with 5N HCl and extracted by shaking with ethylacetate. This solution is then washed with 1N HCl, saturated aqueous NaHCO$_3$ and water, dried over MgSO$_4$ and concentrated by evaporation. The title product is purified by chromatography over kieselgel (eluant: toluene/ethylacetate; 10/1) or recrystallisation (from toluene/petroleum ether) m.p. 85°–88°.

(b) 6-Chloro-4-chloromethyl-2H-1-benzopyrane

A solution of 2.86 g of 6-chloro-4-hydroxymethyl-2H-1-benzopyrane in 50 ml of ether is reacted with 2 ml of pyridine. To the resulting mixture are then slowly added dropwise, with cooling by ice/water, 1.71 g of thionylchloride in 10 ml of diethylether. Reaction is continued for 5 hours at room temperature, the mixture poured onto ice/water and the ether phase separated. This is then washed with saturated aqueous NaHCO$_3$ and water, dried over MgSO$_4$ and concentrated by evaporation. The product is used directly for further reaction.

(c) N-(6-chloro-2H-1-benzopyran-4-yl)-methylamine 500 ml of 33% ethanolic methylamine are added dropwise with cooling by ice/water to 105 g of 6-chloro-4-chloromethyl-2H-1-benzopyrane. Reaction is continued for 8 hours at room temperature, the mixture concentrated by evaporation and the residue taken up in dichloromethane. This solution is washed with 500 ml each of 1N NaOH and water, dried over MgSO$_4$ and concentrated by evaporation. Distillation of the residue yields the title product b.p.: 116–120/13.3 Pascal.

| NMR (CDCl$_3$): | 6,55–7,30 (m, 3H); 5,6–5,9 (m, 1H); 4,62–4,86 (m, 2H); 3,5 (d,J = 1,5Hz, 1H); 2,5 (s, 3H); 1,23 (s, 1H). |
|---|---|

(d) trans-N-(6-chloro-2H-1-benzopyran-4-yl-methyl)-N-methyl-pent-2-en-4-ynyl-1-amine (procedure analogous to Example 2)

(C) (3-benzo[b]thiophenemethyl)methylamine (for Example 7)

Procedure analogous to Example (B)(c) b.p. 90°–94°/13.3 Pascal.

(D) (7-benzo[b]thiophenemethyl)methylamine (for Example 6)

Procedure analogous to Example (B)(c) b.p. 106°–109°/13.3 Pascal.

Formulae drawing sheet 1

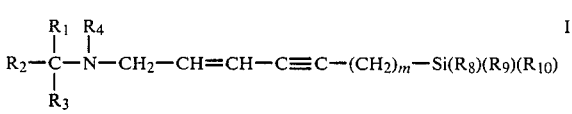  I

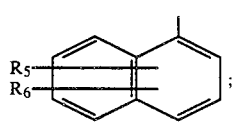  IIa

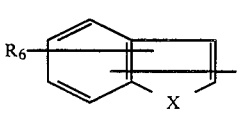  IIb

-continued
Formulae drawing sheet 1

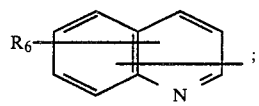  IIc

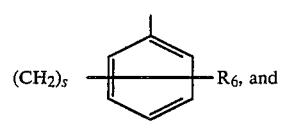  IIId

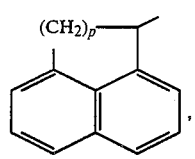  IIe

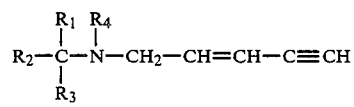  IV $$A{-}(CH_2)_m{-}Si(R_8)(R_9)(R_{10}) \qquad V$$

Formulae drawing sheet 2

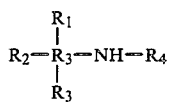  VI

  VII

  VIII

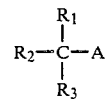  IX $$R_4{-}NH_2 \qquad X$$

We claim:
1. A compound of the formula I:

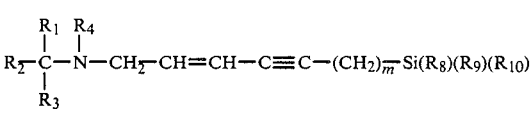  I wherein R$_1$ represents a group of formula IIa, IIb, IIc or IId:

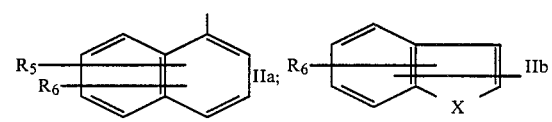

-continued

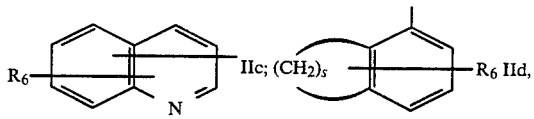

R$_2$ represents hydrogen or lower alkyl or,

R$_1$ and R$_2$ together with the carbon atom to which they are attached represent a group of formula IIe,

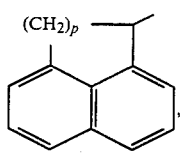

R$_3$ and R$_4$ represent independently hydrogen or lower alkyl or, when R$_1$ represents a group of formula IIa, IIb, IIc or IId, can also represent together a straight-chain C$_3$–C$_5$ alkylene bridge, R$_8$, R$_9$ and R$_{10}$ represent independently lower alkyl or lower alkenyl, and m is 0, 1 or 2, R$_5$ and R$_6$ represent independently hydrogen, halogen, lower alkyl, lower alkoxy or trifluoromethyl, X represents oxygen, sulphur, —O—CH$_2$—, —S—CH$_2$—, —CH$_2$— or —N(R$_7$)—, wherein R$_7$ represents hydrogen or lower alkyl, p is 1, 2 or 3 and s is 3, 4 or 5, or an acid addition salt thereof.

2. A chemotherapeutic composition comprising a compound of formula I as claimed in claim 1 or a chemotherapeutically acceptable acid addition salt thereof together with a chemotherapeutically acceptable diluent or carrier.

3. The compound of claim 1 which is Trans-N-(1-naphthylmethyl)-N-methyl-5-trimethylsilyl-pent-2-en-4-ynyl-1-amine.

4. A compound of claim 1, which is trans-N-(1-naphthylmethyl)-5-trimethylsilyl-pent-2-en-4-ynyl-1-amine.

5. A compound of claim 1 in which R$_1$ is a group of the formula IIa or IIb, R$_2$, R$_3$ and R$_6$ are each hydrogen, R$_4$ is lower alkyl, R$_5$ is hydrogen or halogen, R$_8$, R$_9$ and R$_{10}$ are each alkyl, m is O and X is O or S.

* * * * *